(12) United States Patent
Marino et al.

(10) Patent No.: US 12,173,268 B2
(45) Date of Patent: Dec. 24, 2024

(54) MULTI-WELL MECHANICAL STIMULATION SYSTEMS AND INCUBATORS

(71) Applicants: University of Pittsburgh—Of the Commonwealth System of Higher Education, Pittsburgh, PA (US); Fondazione Ri.MED, Palermo (IT)

(72) Inventors: Davide Marino, Paternò (IT); Riccardo Gottardi, Pittsburgh, PA (US); Rocky Sung Chi Tuan, Pittsburgh, PA (US)

(73) Assignees: University of Pittsburgh—Of the Commonwealth System of Higher Education, Pittsburgh, PA (US); Fondazione Ri.MED, Palermo (IT)

( * ) Notice: Subject to any disclaimer, the term of this patent is extended or adjusted under 35 U.S.C. 154(b) by 1301 days.

(21) Appl. No.: 16/753,710

(22) PCT Filed: Oct. 19, 2018

(86) PCT No.: PCT/US2018/056715
§ 371 (c)(1),
(2) Date: Apr. 3, 2020

(87) PCT Pub. No.: WO2019/079722
PCT Pub. Date: Apr. 25, 2019

(65) Prior Publication Data
US 2020/0270561 A1    Aug. 27, 2020

Related U.S. Application Data

(60) Provisional application No. 62/574,664, filed on Oct. 19, 2017.

(51) Int. Cl.
*C12M 1/42*    (2006.01)
*C12M 1/00*    (2006.01)
(Continued)

(52) U.S. Cl.
CPC ............ *C12M 35/04* (2013.01); *C12M 23/12* (2013.01); *C12M 23/38* (2013.01); *C12M 27/00* (2013.01);
(Continued)

(58) Field of Classification Search
CPC ....... C12M 23/12; C12M 41/14; C12M 1/005
(Continued)

(56) References Cited

U.S. PATENT DOCUMENTS

| 4,511,534 A | * | 4/1985 | Bennett, Jr. | ......... B01L 3/50853 422/922 |
| 4,626,509 A | | 12/1986 | Lyman | |

(Continued)

FOREIGN PATENT DOCUMENTS

| DE | 4104831 | * 10/1992 |
| WO | WO 2014/078379 | 5/2014 |
| WO | WO 2017/062629 | 4/2017 |

OTHER PUBLICATIONS

Extended European Search Report for related EP Application No. 18868400.5, 7 pages, mailed Jun. 16, 2021.
(Continued)

*Primary Examiner* — Holly Kipouros
*Assistant Examiner* — Nathan G Esperon
(74) *Attorney, Agent, or Firm* — Klarquist Sparkman, LLP (57) ABSTRACT

Disclosed mechanical stimulator systems can maintain the sterility of biological samples within a multi-well plate while mechanically stimulating the samples. The systems disclosed herein allow for the individual activation by mechanical compression of a high number of samples at the same time, while maintaining sterility of the samples. The well plates, guides, actuators, pistons, and other components of the disclosed systems can be configured to be contained
(Continued)

in or adjacent to an incubator that can control properties such as gas levels and temperature while at the same time allowing for the mechanical actuation of the biological samples.

20 Claims, 12 Drawing Sheets

(51) Int. Cl.
    *C12M 1/02*     (2006.01)
    *C12M 1/12*     (2006.01)
    *C12M 1/32*     (2006.01)
    *C12M 1/34*     (2006.01)
    *C12N 5/00*     (2006.01)

(52) U.S. Cl.
    CPC ............ *C12M 37/04* (2013.01); *C12M 41/12* (2013.01); *C12M 41/34* (2013.01); *B01L 2400/0478* (2013.01); *C12N 5/0068* (2013.01)

(58) Field of Classification Search
    USPC ............................................ 435/305.2, 305.3
    See application file for complete search history.

(56) References Cited

U.S. PATENT DOCUMENTS

| | | | |
|---|---|---|---|
| 2008/0199365 A1 | 8/2008 | Chu | |
| 2010/0009335 A1* | 1/2010 | Joseph | C12M 23/22 435/286.1 |
| 2013/0099407 A1* | 4/2013 | Tully | C12M 23/12 425/84 |
| 2016/0201037 A1* | 7/2016 | Tuan | C12M 23/34 435/373 |

OTHER PUBLICATIONS

International Search Report and Written Opinion for related International Application No. PCT/US2018/056715, 7 pages, mailed Dec. 14, 2018.

"Communication—European Examination Report" from the European Patent Office for European Application No. EP18868400.5-1014, dated Apr. 19, 2024, 4 pages.

* cited by examiner

MULTI-WELL MECHANICAL STIMULATION SYSTEMS AND INCUBATORS

CROSS-REFERENCE TO RELATED APPLICATIONS

This application is the U.S. National Stage of International Application No. PCT/US2018/056715 filed Oct. 19, 2018, which claims the benefit of U.S. Provisional Application No. 62/574,664 filed Oct. 19, 2017, which is incorporated by reference herein in its entirety.

This application is related to the disclosure of International Patent Application No. PCT/US2016/055763 filed on Oct. 6, 2016, published as WO 2017/062629 A1 on Apr. 13, 2017, which is incorporated herein by reference in its entirety. This application is also related to the disclosure of International Patent Application No. PCT/US2014/052348 filed on Aug. 22, 2014, published as WO 2015/027186 A1 on Feb. 2, 2015, which is incorporated herein by reference in its entirety. The currently disclosed technology can be applied to or in combination with the exemplary bioreactors and microfluidic tissue development systems described in WO 2015/027186 A1 and WO 2017/062629 A1, for example, or to various other systems where multi-well plates are used to hold a plurality of biological samples.

FIELD

This application relates to the multi-well plates for biological samples, mechanical stimulation systems therefore, and incubators therefor.

SUMMARY

Disclosed herein are embodiments of mechanical stimulator systems that can, among other things, maintain the sterility of biological samples within a multi-well plate while mechanically stimulating the samples. The systems disclosed herein allow for the individual activation by mechanical compression of a high number of samples at the same time, while maintaining sterility of the samples. The well plates, guides, actuators, pistons, and other components of the disclosed systems can be configured to be contained in or adjacent to an incubator that can control properties such as gas levels and temperature while at the same time allowing for the mechanical actuation of the biological samples.

DETAILED DESCRIPTION

Figure 1:
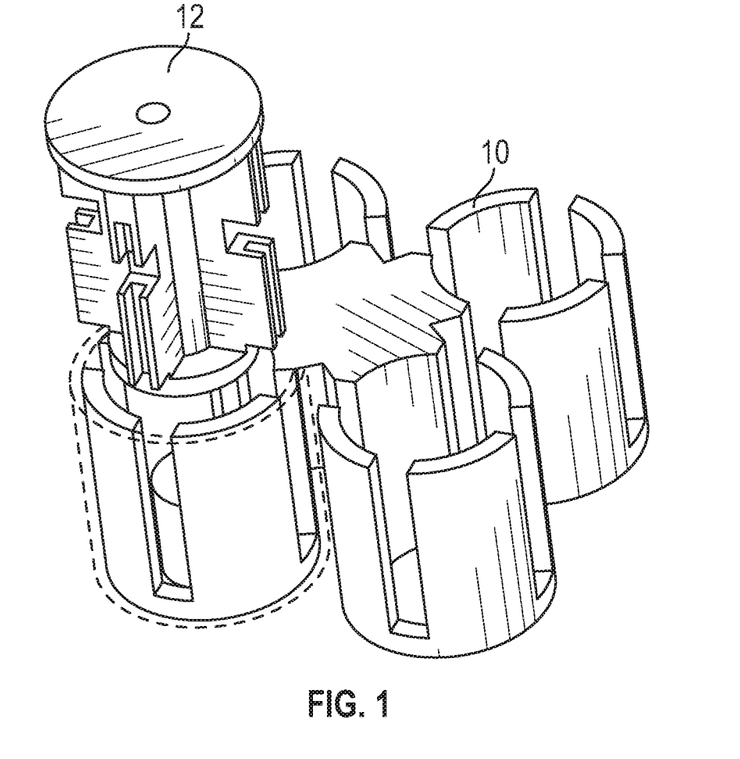
FIG. 1 shows an exemplary group of four guides configured to receive four pistons, one of which is shown.
Figure 2:
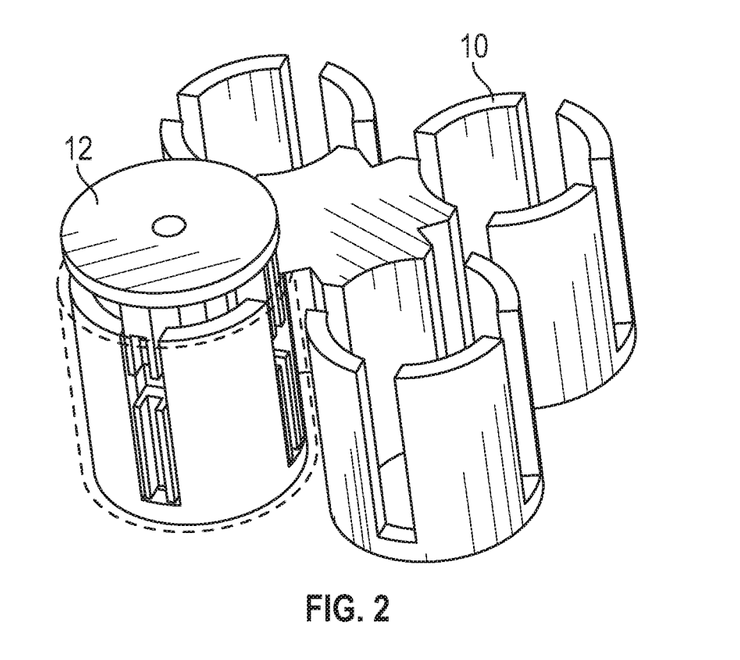
FIG. 2 shows the piston inserted into the guide of FIG. 1.
Figure 3:
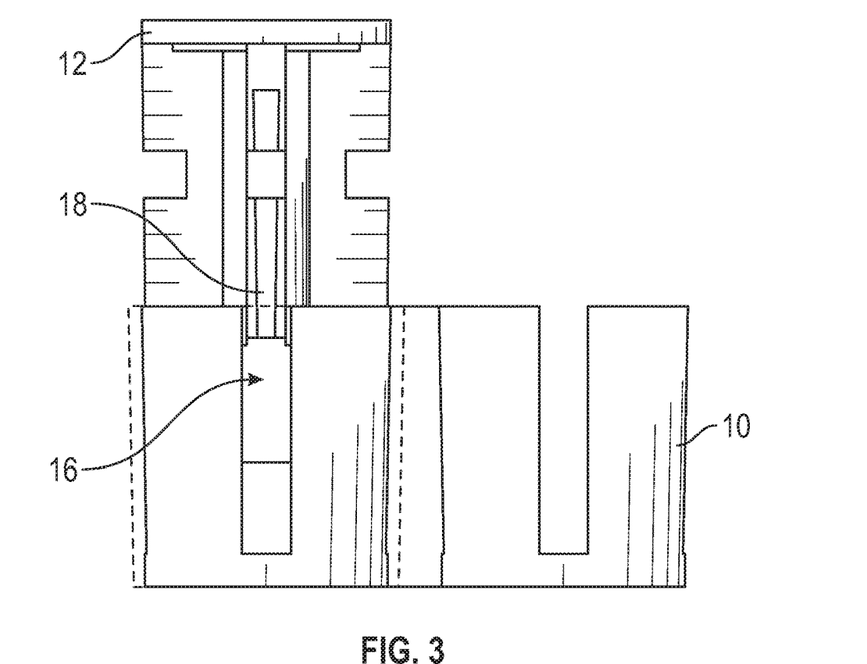
FIG. 3 is a side elevation view of FIG. 1.
Figure 4:
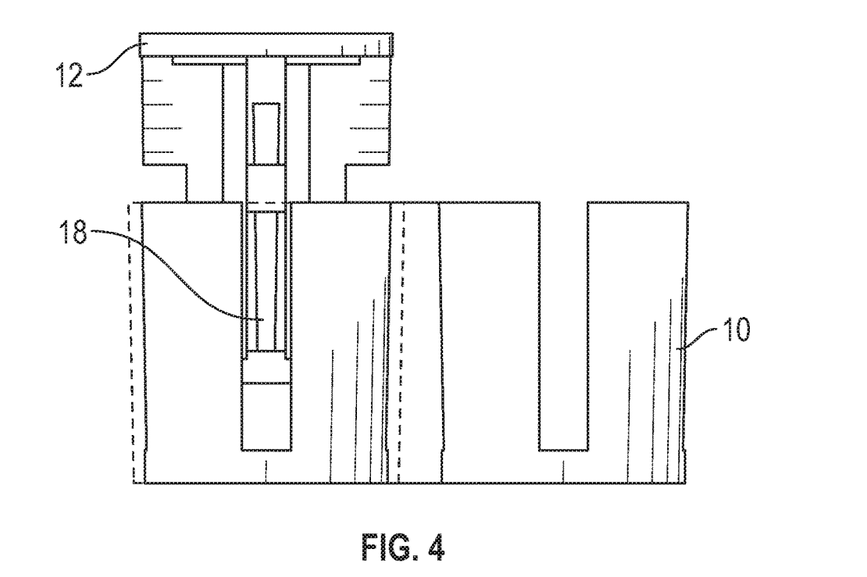
FIG. 4 is a side elevation view of FIG. 2.
Figure 5:
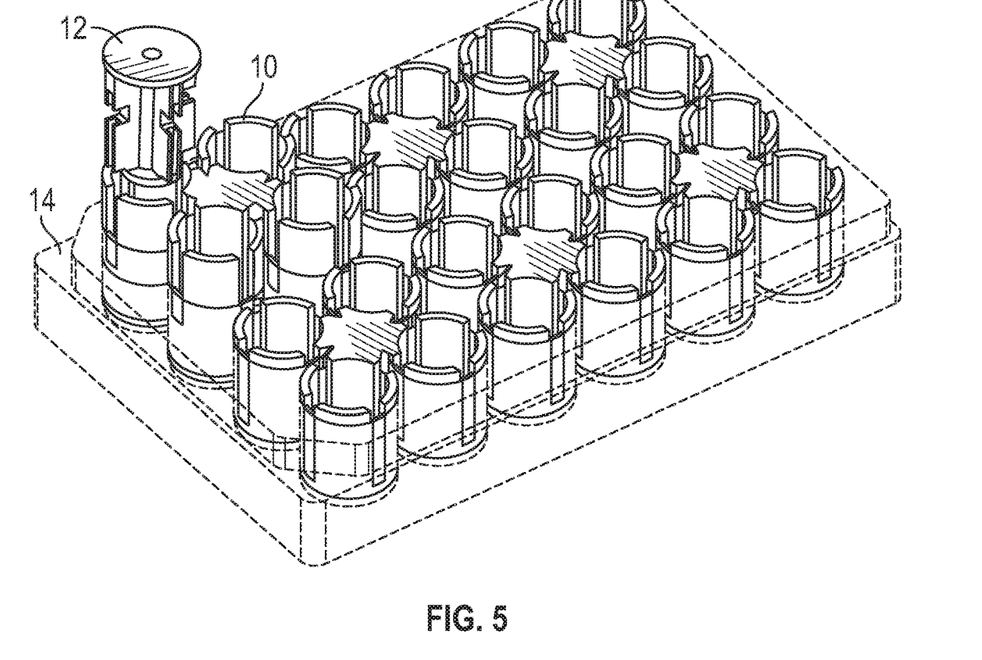
FIG. 5 shows a 24-well plate holding six of the groups of four guides of FIG. 1.
Figure 6:
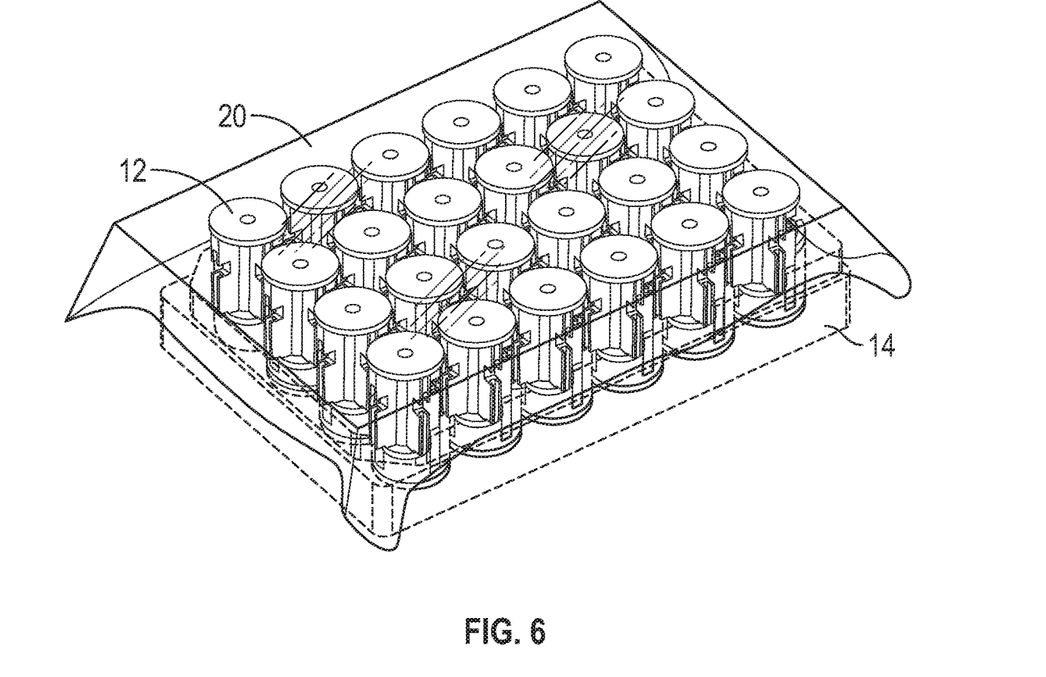
FIG. 6 shows the 24-well plate of FIG. 5 with 24 pistons above the guides and a protective membrane over the pistons.

An exemplary mechanical stimulator system is illustrated in FIGS. 1-14. Some exemplary systems can comprise a tissue culture 24-well plate 14 and a mechanical stimulator system comprising specially configured guides 10 that are inserted into the wells of the plate 14. While examples are described herein with regard to conventional 24-well plate, the disclosed technology can analogously be applied to any multi-well plate configuration, such as 96-well plates, etc. The guides 10 can help maintain the correct position of mechanical actuation pistons 12 that extend through the guides and are directly in contact with the tissue culture samples in the wells, such that the pistons are configured to stimulate the samples. The guides 10 can be coupled together in groups (e.g., groups of four as shown, groups of 24, etc.). As shown in FIGS. 3 and 4, the guides 10 can have slots 16 along their sides that receive corresponding projections 18 of the pistons 12 to align and guide the pistons along a vertical path of motion relative to the wells.

In some embodiments, the multi-well plate 14 can be made of polystyrene (e.g., crystal grade), treated with vacuum gas plasma to make the internal bottom surface hydrophilic (wettable) and suitable for cell attachment.

The actuating pistons 12 can have any one or more of the following features:

1. The volume of the pistons can be relatively small compared to the volume of the wells to avoid squishing out the media from the wells; and
2. Grooves/open spaces in the pistons can favor/facilitate the inflow and outflow of media to and from the well during the mechanical stimulation. For example, the pistons can include vertical channels for excess fluid to flow when the piston moves down into the well. The vertical channels can be located with each of the four flanges of the piston. At the top of the vertical channels can be lateral openings in the four flanges, to allow the displaced fluid to flow out of the flanges and into open spaces between the four flanges, the outside of the central shaft, within the guides, and above the lower flat disc of the piston that contacts the sample. When the piston moves back up from the sample, lower pressure it causes in the well can draw the fluid back through the channels in the piston and back into the space below the piston in the well. The pistons can fit snuggly in the guides and wells so that the displaced fluid stays in the well and just shifts back and forth through the channels in the pistons.

The guides 10 can have any one or more of the following features:

1. The bottom part of the guides can keep the constructs within the stimulated area of the pistons in order to perform a semi-confined compression;
2. The height of the bottom part of the guides may stop or limit the insertion depth of the pistons to avoid the overstressing of the constructs if certain problems of the system occur. In some embodiments, the maximum displacement of the pistons can be adjusted/chosen by changing the height of the bottom part of the guides; and
3. The guides can be coupled together in groups (e.g., as shown) or be individually supported in the wells. When formed in groups, there can be coupling elements that extend over the tops of the wells and attach to each of the adjacent guides. This can facilitate placement and removal of the guides, and can keep the guides properly oriented relative to each other and relative to the wells.

In order to guarantee the sterility inside the wells, all pistons 12 can be attached to a membrane that acts as a cover to avoid any bacterial penetration. An exemplary protective membrane 20 is shown in FIGS. 6-12.

Figure 7:
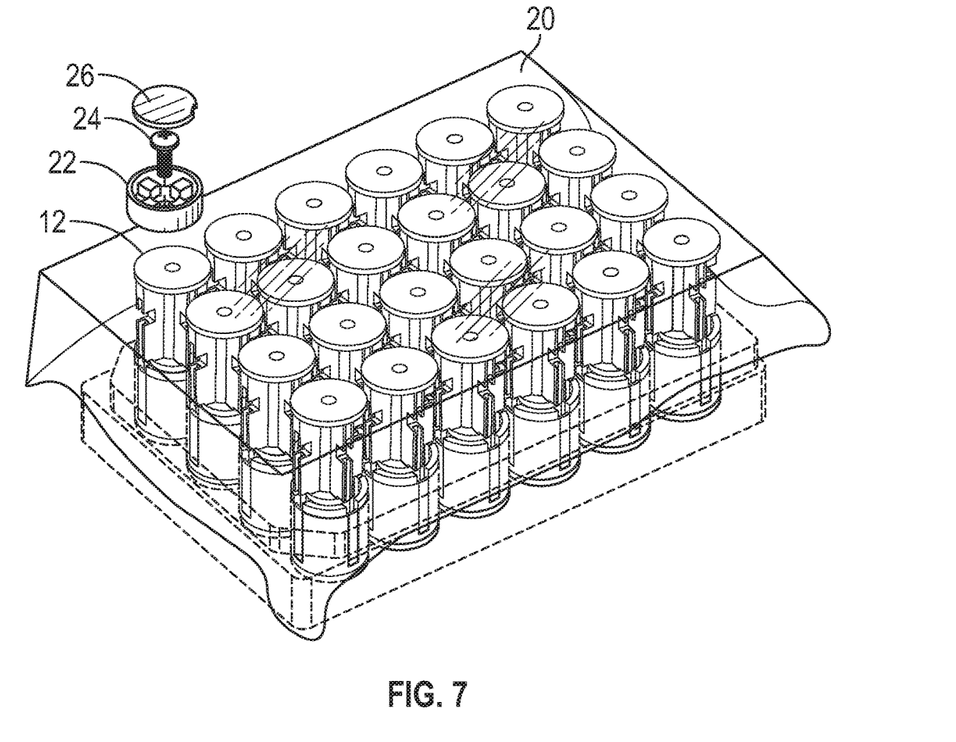
FIG. 7 shows the system of FIG. 6 with one piston support shown above the membrane.
Figure 8:
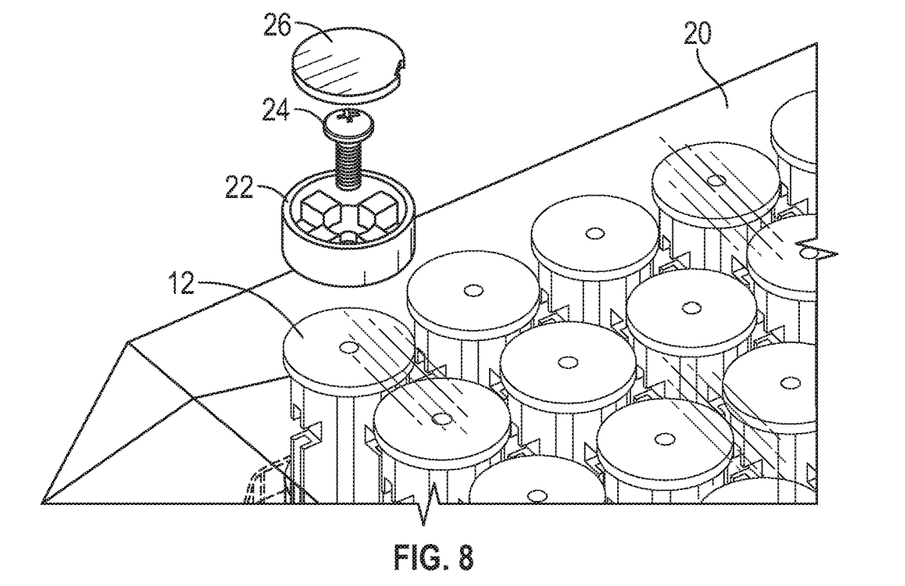
FIG. 8 is an enlarged view of FIG. 7.
Figure 9:
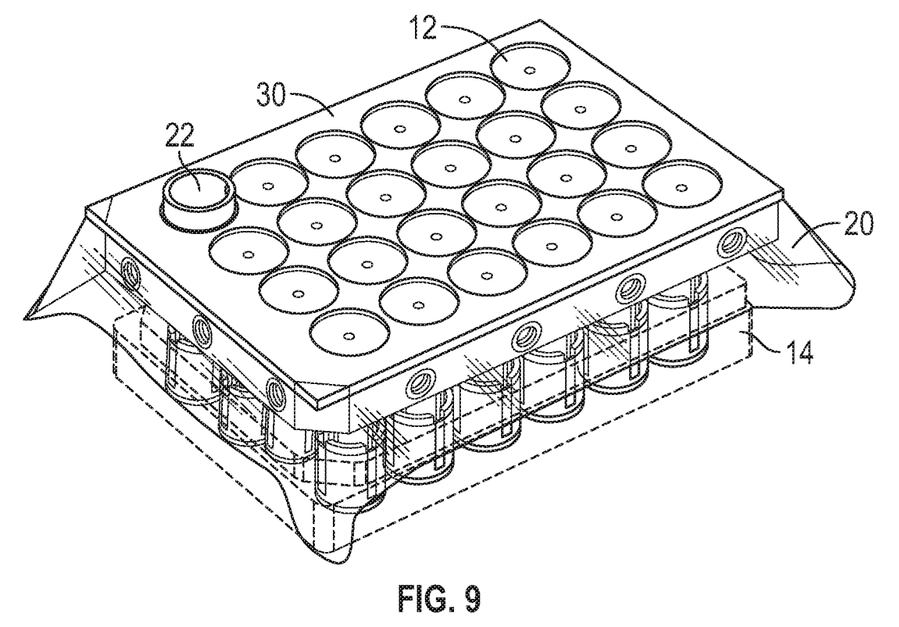
FIG. 9 shows the system of FIG. 7 with a holed lid that holds the membrane positioned over the pistons.
Figure 10:
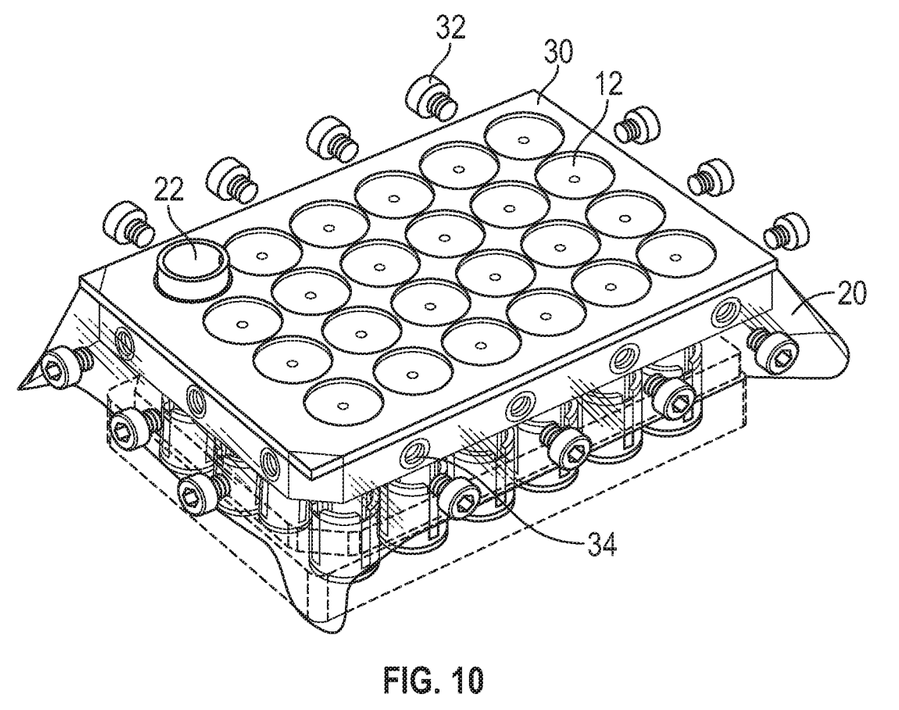
FIG. 10 shows the system of FIG. 9 with fasteners around the perimeter of the holed lid.
Figure 11:
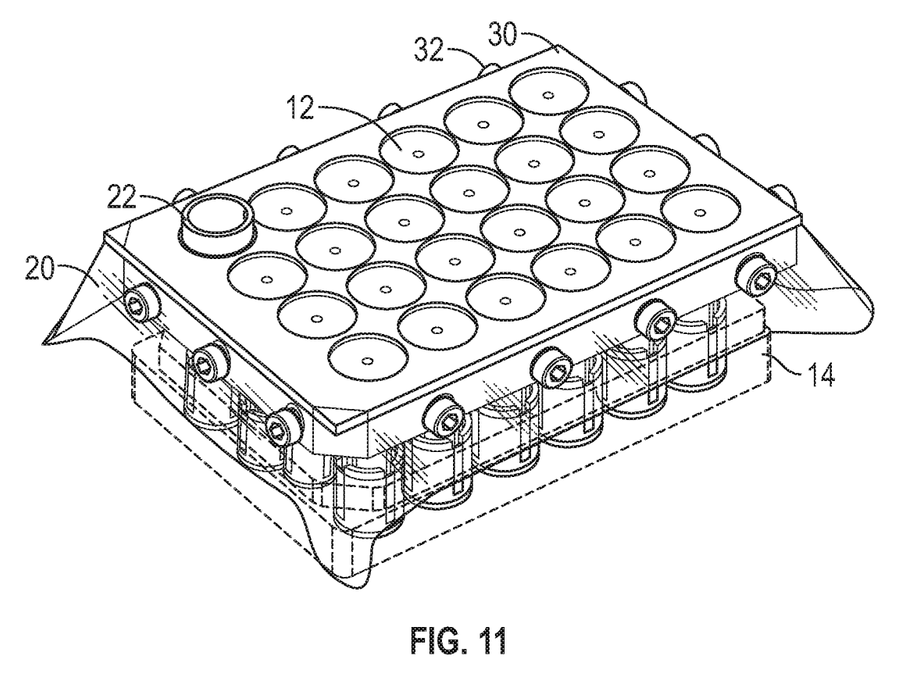
FIG. 11 shows the system of FIG. 10 with the fasteners inserted into the sides of the holed lid.

The membrane 20 can be compressed between the upper surfaces of the pistons 12 and a plurality of piston supports 22 (e.g., one support for each piston), the form of which can be such that a screw 24 can merge the three objects (piston, membrane, support) together. A small lid 26 can be put on top of the support 22 over the head of the screw 24 in order to make the upper surface contact as flat as possible and without defects or hole, as shown in FIGS. 7-8.

The membrane 20 can be very flexible. To make the structure as solid as possible, the membrane 20 can be pinned to the sides of a holed lid 30, as shown in FIGS. 9-13, such as with screws 32. The holed lid 30 can have threaded holes 34 on the sides where the screws 32 may be inserted. The lid can comprise an upper plate and a lower plate, for example, and the membrane can be sandwiched between the upper and lower plates. The two plates can each have aligned holes to accommodate the pistons 12. The two plates can be secured together arounds the sides, for example, with screws to lock the membrane in place. For example, the upper plate can have a lip that goes over the edges of the lower plate and the screws 32 can pass through the lip into the lower plate. Thus, the membrane 20 can be fixed between the two lid plates and also fixed between each piston and its support.

Figure 12:
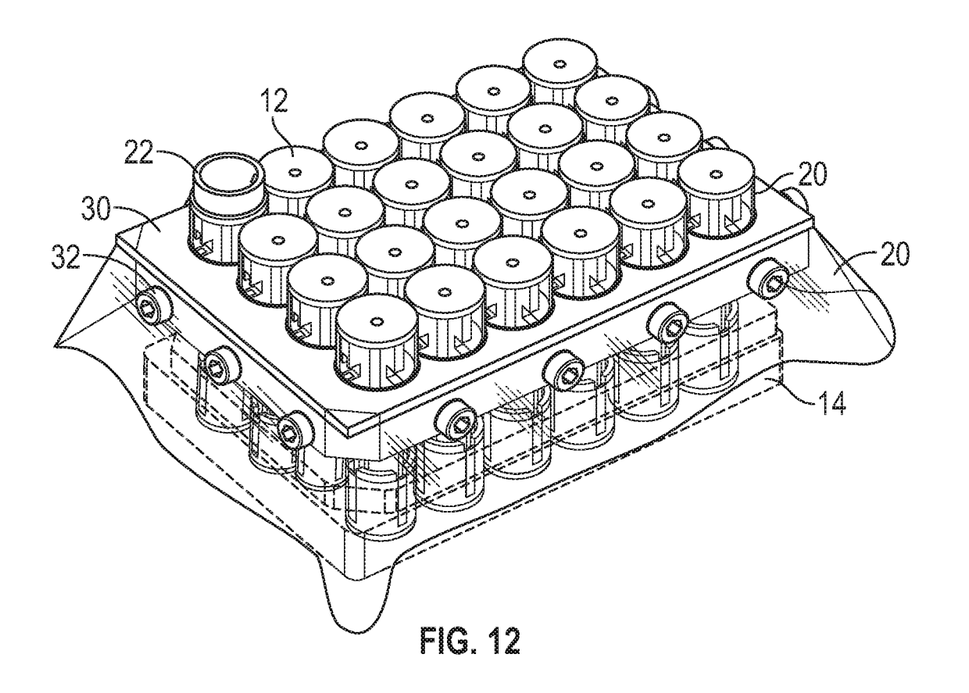
FIG. 12 shows the system of FIG. 11, with the holed lid moved down over the pistons.

In this arrangement, the membrane 20 can potentially interfere with the movement of the pistons 12 with an opposite force depending on its elastic properties. To minimize this effect, the membrane 20 can be permanently stretched out (e.g., pre-deformed or manufactured with specific pockets or deformations) sufficiently to allow the pistons 12 to go up and down without substantial additional force applied by the membrane. For example, the membrane can have 24 individual pockets that extend up from the plane of the lid to accommodate the pistons protruding up above the lid. This is illustrated in FIG. 12.

A very stretchable nylon membrane can be used, as one example. As the pistons actuate downward, the membrane pockets around the pistons can deform (e.g., compress down, wrinkle, bulge, etc.) a small amount to accommodate the downward actuation.

The mechanical and physicochemical properties of an exemplary nylon membrane are shown below:

| Material | Grade | Texture | Color | Thickness | Hardness | Maximum temperature |
|---|---|---|---|---|---|---|
| Nylon plastic | 6/6 | Smooth | Semi-clear off-white | 0.05 ± 0.01 mm | Rockwell R110 | 230° C. |

| Impact strength | Tensile strength | Density | Water absorption | Coefficient of thermal expansion |
|---|---|---|---|---|
| 320 J/m | 77 MPa | 1134 kg/m3 | 1.35% | $8.6 \times 10^{-5}$ |

Figure 13:
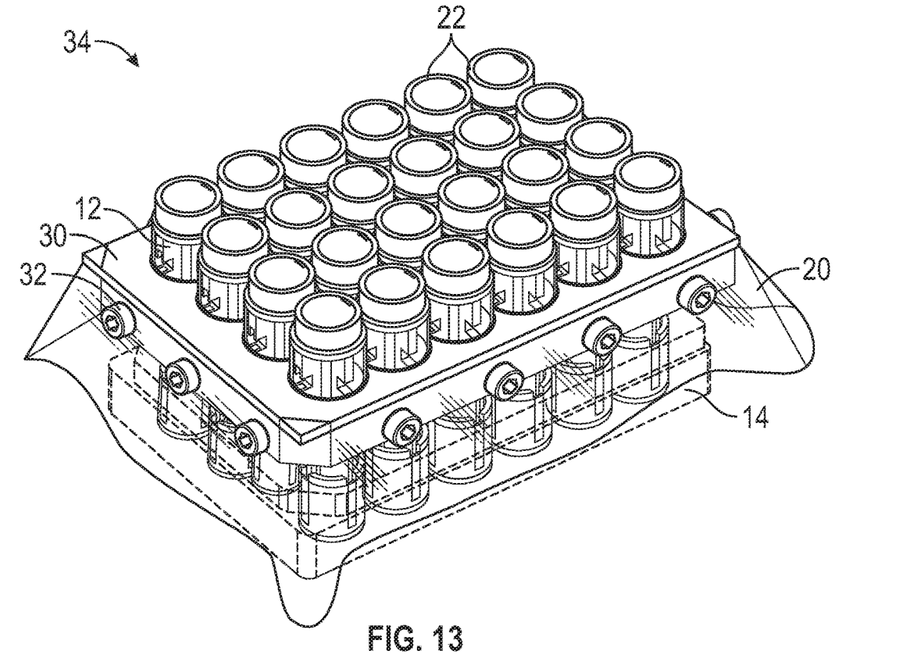
FIG. 13 shows the system of FIG. 12 with 24 pistons supports attached to the tops of the 24 pistons.
Figure 14:
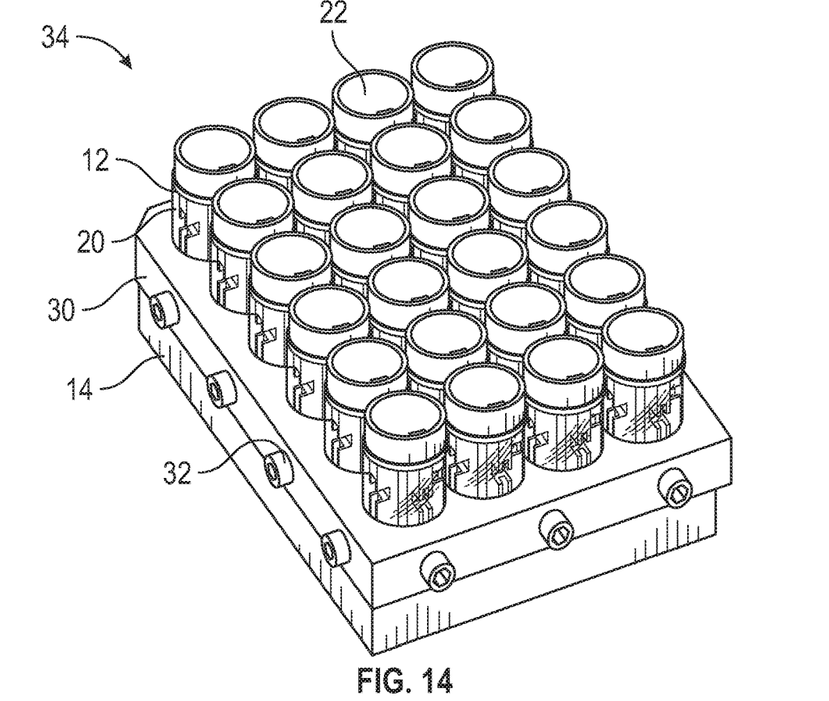
FIG. 14 shows another example of the system of FIG. 13.

An exemplary system 34 with the pistons 12, supports 22, lid plates 30, and membrane 20 is shown in FIGS. 13 and 14.

The upper surfaces of the supports 22 can be flat to receive forces from an actuation mechanism (not shown, see WO 2015/027186 A1 and WO 2017/062629 A1, for examples). The actuation mechanism can include 24 individual actuators, one dedicated for each piston 12, or six actuators can shift laterally in a pattern to cycle between four different groups of six pistons, or one actuator that contacts all 24 or groups of six or four pistons, for example. Any type of actuation mechanism can be used, and any cyclic pattern or actuation can be used. The pistons 12 can recoil back up due to pressure inside the wells after the actuation mechanism pushes them down. In some embodiments, the tops of the pistons/supports can be coupled to the actuation mechanism such that the actuation mechanism can forcibly pull the pistons back up, as well as pushing them down. In such embodiments, the actuation mechanism can be permanently coupled or selectively detachable from the tops of the pistons/supports, such as with a mechanical linkage or an electromagnetic connection that allows for rapid connection and detachment based on an electrical signal.

Figure 15:
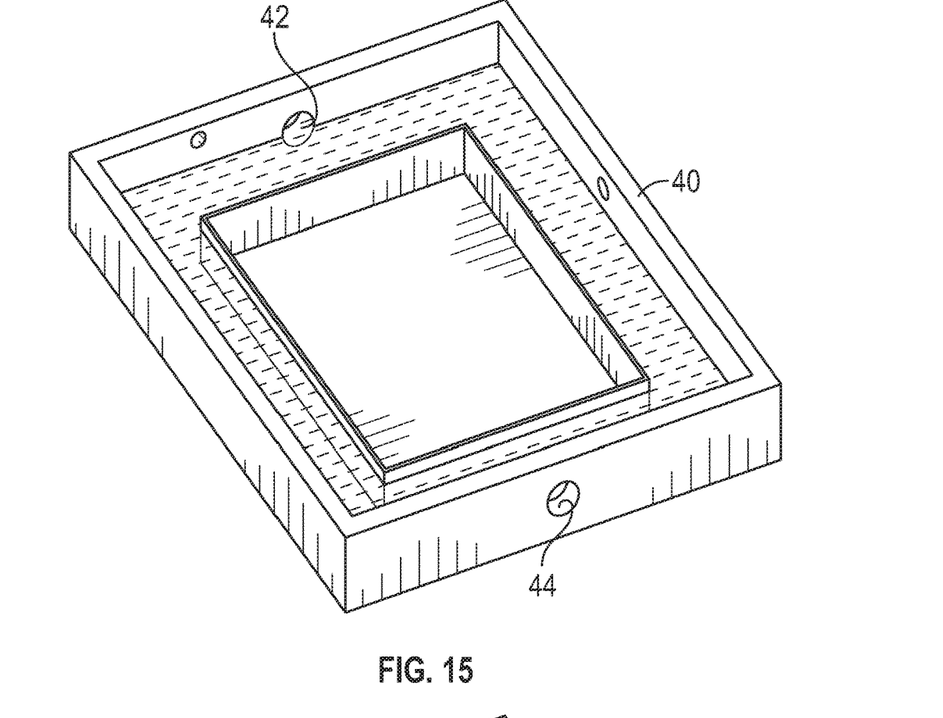
FIG. 15 shows an exemplary incubator.
Figure 16:
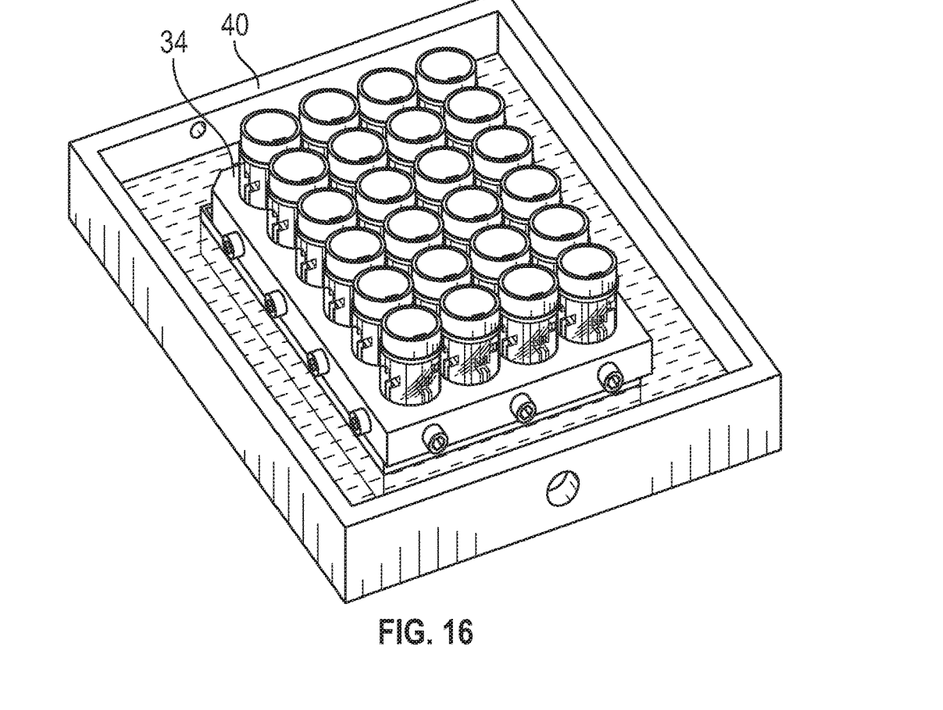
FIG. 16 shows the incubator of FIG. 15 with the system of FIG. 14 inside the incubator.
Figure 17:
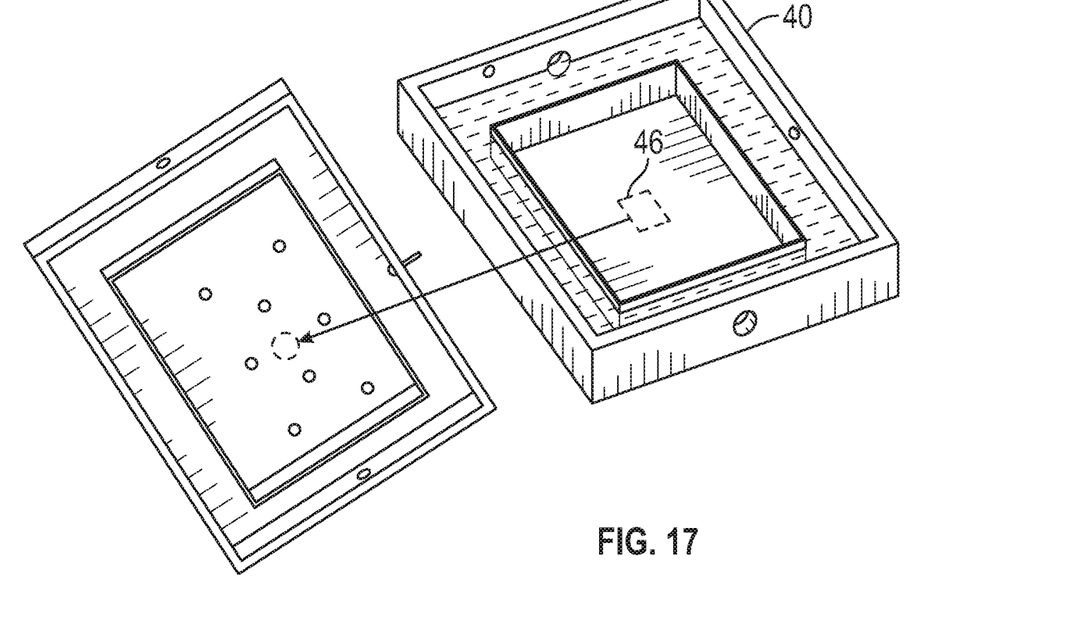
FIG. 17 shows an incubator that includes a temperature sensor.

Once the system 34 has been built, it can be very easy to sterilize, such as with ethanol, since there are no holes through the membrane in which the liquid may be trapped. Moreover, the system may need to be sterilized only once (e.g., before each cycle of stimulation), since it may be easily stored in another 24-well plate after every stimulation. Other requirements to stimulate engineered or native tissue may include physiologic temperature maintenance and/or CO2 or other gas level maintenance A specialized incubator can be used to satisfy these requirements. An exemplary incubator 40 is illustrated in FIGS. 15-16, without and with the system 34 of FIGS. 13 and 14 inserted inside the incubator. Such an incubator 40 can comprise a box or other housing configured to include a temperature-controlled water flux (or other fluid) having a water inlet 42 and water outlet 44 to maintain/regulate the temperature of a base in which may be inserted a well plate 14. The volumetric flow rate of the water flux can be controlled by an external water pump. The water flux can be controlled by a feedback control with a temperature sensor 46 placed underneath the base, as illustrated in the FIG. 17.

Figure 18:
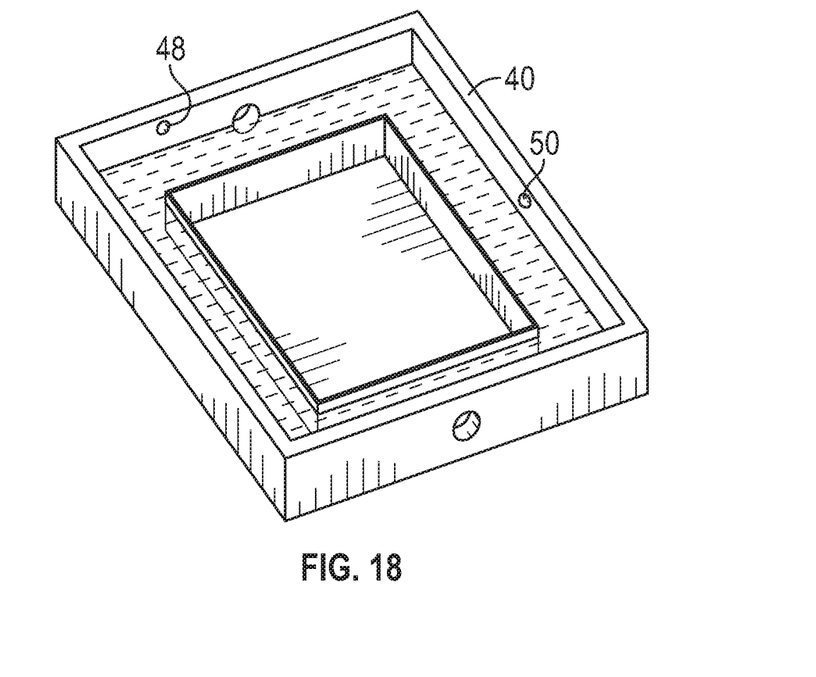
FIG. 18 shows an incubator that includes a $CO_2$ inlet and sensor.
Figure 19:
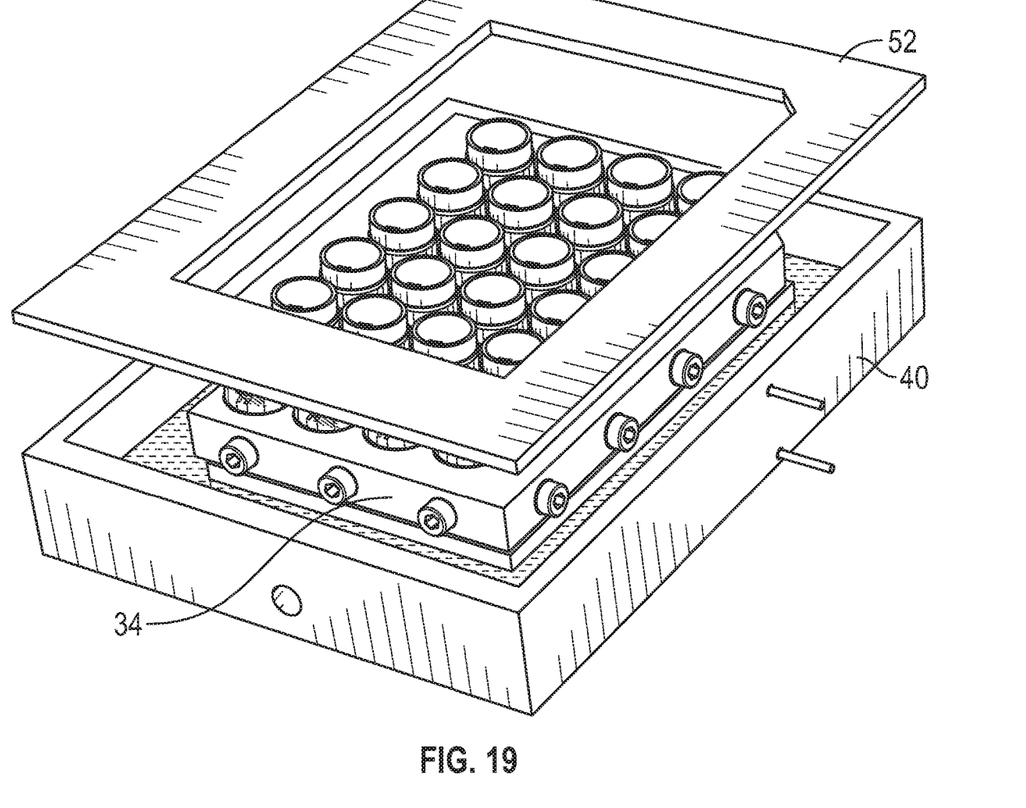
FIG. 19 shows a lid placed over the incubator of FIG. 16.
Figure 20:
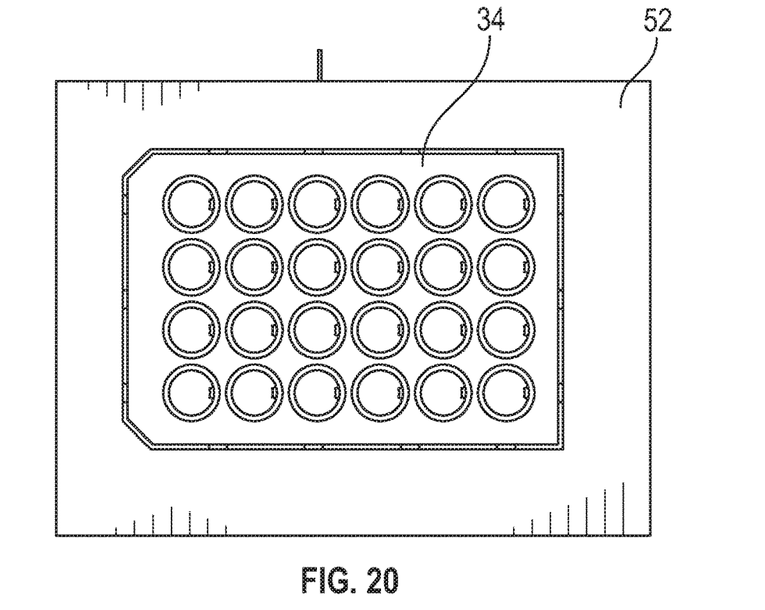
FIG. 20 is a top view of FIG. 19.
Figure 21:
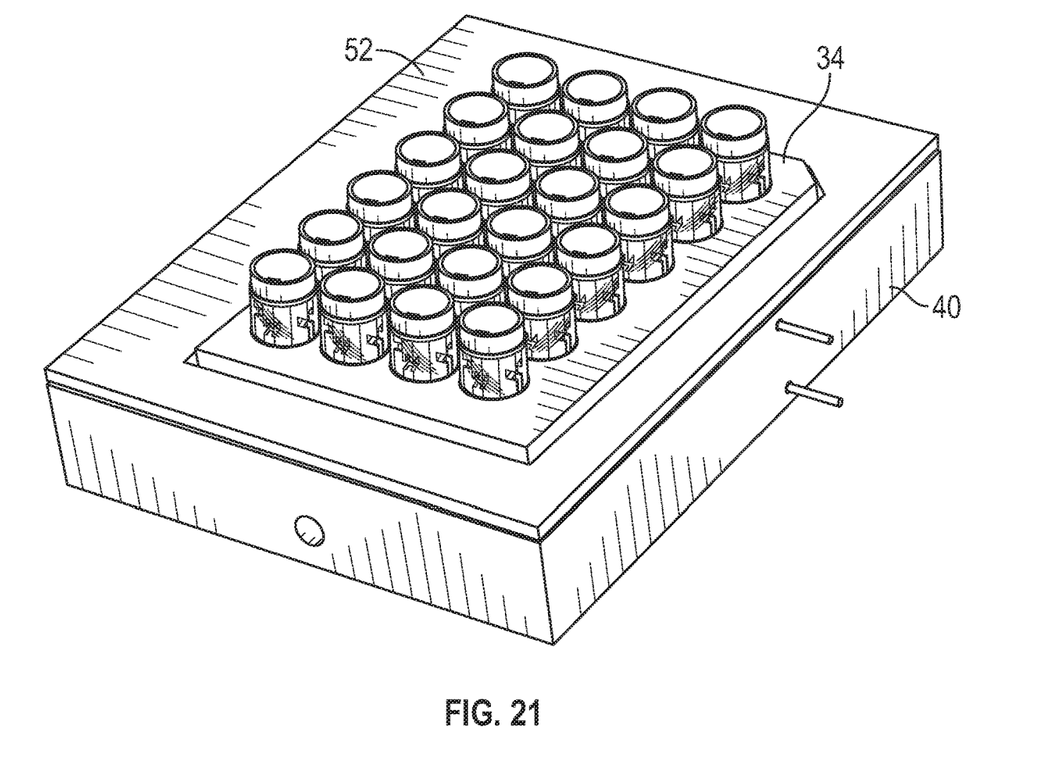
FIG. 21 shows the lid lower over the pistons and coupled to the top of the incubator.

The carbon dioxide level can be managed by a $CO_2$ inlet 48 and sensor 50 placed in the upper part of the incubator, for example. Another feedback control can regulate the flux of an external $CO_2$ pump, as illustrated in FIG. 18.

Finally, an incubator lid 52 can be included that covers the incubator 40 to create a closed environment around the system 34, as illustrated in FIGS. 19-22. A cross-section of the assembled incubator 40 and system 34 is shown in FIG.

Figure 22:
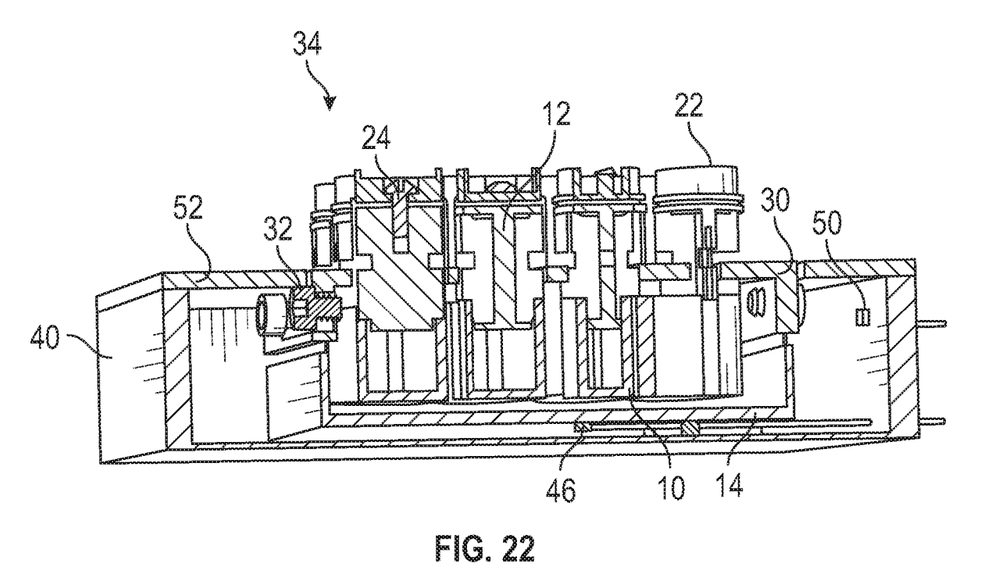
FIG. 22 is a cross-sectional side view of the assembled system of FIG. 21.

22, showing the sample chambers under the pistons and the incubator interior around and below the well plate 14.

In some embodiments, the incubator can be configured to avoid the possibility that the fluid from the incubator gets in contact with the well plate and/or in contact with the tissue samples. For example, in some embodiments the incubator is divided in two separated monophasic spaces: gas and fluid. The incubator can be divided by a septum in correspondence of the edges of the base where the 24-well plate can be inserted. In this way, the water flux can be more controlled because the volume of the space available for the water transfer is constant and separated from the plate. In other embodiments, the fluid in the incubator can be kept separate from the wells/tissue samples by other means, such as other physical wall formations, gaskets, membranes around the well plate, etc.

In some embodiments, the mechanical actuation systems can be configured to mimic real-world biological stimulations, such as the impacts on joints caused by walking or running. For example, the pistons can be reciprocated at about 1 Hz to simulate slow walking. This can be used with cartilage and/or bone samples in the wells, for example, to simulate human knee joint conditions or similar joint physiology. In some such examples, the pistons can reciprocate about 0.13-0.16 mm (or about 15% of initial height). In other examples, the pistons can reciprocate about 50% of initial height. The amount of compression applied to the tissue samples can cause about 10% strain to simulate physiological stress conditions, or can cause about 40-50% strain to simulate excessive loading, or can cause other stress levels as desired. The stimulation can applied for 40 seconds, 1800 seconds, or other desired durations. Using the disclosed systems, it can be possible to determine properties of the biological samples in the wells, such as Young's Modulus and viscoelastic behavior properties, and the changes in such properties over time as the materials are mechanically stimulated.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Characteristics and features described in conjunction with a particular aspect, embodiment, or example of the disclosed technology are to be understood to be applicable to any other aspect, embodiment or example described herein, or in the references incorporated by reference herein, unless incompatible therewith. All of the features disclosed in this specification (including any accompanying claims, abstract and drawings) and in the incorporated references, and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings) and incorporated references, or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the included figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of the following claims.

The invention claimed is:

1. A system, comprising:
a plurality of guides configured to be inserted into wells of a multi-well plate, the wells being configured to contain biological samples;
a plurality of pistons configured to fit into the guides and reciprocate within the guides to provide mechanical stimulation to the biological samples in the wells;
a plurality of supports coupled to upper ends of the pistons, wherein the supports are configured to interface with a mechanical actuation mechanism to drive the pistons; and
a membrane that passes between the supports and the pistons and spans across upper sides of the pistons and is sized to cover the multi-well plate when the system is applied to the multi-well plate, the membrane providing a shield to maintain sterility of the biological samples in the wells.

2. The system of claim 1, wherein at least some of the guides are attached together in a fixed group of guides spanning multiple wells.

3. The system of claim 1, wherein the guides comprise vertical guide channels to guide vertical reciprocation motion of the pistons within the guides.

4. The system of claim 1, wherein the guides comprise a stop that sets a maximum depth that the pistons can be inserted into the wells.

5. The system of claim 1, wherein the pistons comprise radially extending flanges that interface with the guides to restrict motion of the pistons to vertical reciprocation.

6. The system of claim 1, wherein the pistons comprise vertical channels that allow fluid from the wells to pass up through the pistons when the pistons move down into the wells.

7. The system of claim 6, wherein the pistons comprise open spaces to receive displaced fluid from the wells when the pistons move down into the wells.

8. The system of claim 1, wherein the membrane comprises a plurality of deformed pockets corresponding to locations of the pistons, the pockets allowing reciprocation of the pistons.

9. The system of claim 1, further comprising a lid having holes through which the pistons pass, the lid being secured to the membrane, wherein the lid is configured to cover a top of the multi-well plate and help maintain sterility of the biological samples in the wells.

10. The system of claim 1, further comprising an incubator that at least partially contains the multi-well plate with the guides and pistons coupled to the wells.

11. The system of claim 10, wherein the incubator comprises a fluid inflow port and fluid outflow port and is configured to control a flux of fluid through the wells while the biological samples in the wells are mechanically stimulated by the pistons.

12. The system of claim 10, wherein the incubator comprises a temperature sensor and is configured to control the temperature of the samples in the wells while the samples in the wells are mechanically stimulated by the pistons.

13. The system of claim 10, wherein the incubator comprises a gas sensor and is configured to control gas concentration levels in the wells while the biological samples in the wells are mechanically stimulated by the pistons.

14. The system of claim 10, wherein the incubator is divided in two separated monophasic spaces for gas and liquid.

15. The system of claim 14, wherein the incubator is divided by a septum such that space inside the incubator available for fluid transfer is constant and separated from the multi-well plate.

16. The system of claim 1, further comprising a motorized actuation system that engages the pistons to cause a selected reciprocation motion of the pistons.

17. The system of claim 1, wherein the system is capable of determining a Young's Modulus of viscoelastic biological samples within the wells.

18. A method of mechanically stimulating a plurality of biological samples using the system of claim 1, comprising reciprocating the pistons within the guides to apply mechanical pressure to the biological samples within the wells.

19. A system, comprising:
a plurality of guides configured to be inserted into wells of a multi-well plate, the wells being configured to contain biological samples;
a plurality of pistons configured to fit into the guides and reciprocate within the guides to provide mechanical stimulation to the biological samples in the wells; and
a membrane comprising a plurality of deformed pockets corresponding to locations of the pistons, wherein the membrane spans across upper sides of the pistons and is sized to cover the multi-well plate when the system is applied to the multi-well plate, wherein the membrane provides a shield to maintain sterility of the biological samples in the wells and the pockets are configured to allow reciprocation of the pistons.

20. A system, comprising:
a plurality of guides configured to be inserted into wells of a multi-well plate, the wells being configured to contain biological samples;
a plurality of pistons configured to fit into the guides and reciprocate within the guides to provide mechanical stimulation to the biological samples in the wells;
a membrane that spans across upper sides of the pistons and is sized to cover the multi-well plate when the system is applied to the multi-well plate, the membrane providing a shield to maintain sterility of the biological samples in the wells; and
a lid having holes through which the pistons pass, the lid being secured to the membrane, wherein the lid is configured to cover a top of the multi-well plate and help maintain sterility of the biological samples in the wells.

* * * * *